United States Patent [19]

Blachly, deceased et al.

[11] 4,270,531
[45] Jun. 2, 1981

[54] OROPHARYNGEAL AIRWAY AND BITE BLOCK ASSEMBLY AND METHOD OF USE FOR CLOSED PULMONARY VENTILATION

[76] Inventors: Paul H. Blachly, deceased, late of Portland, Oreg.; By Beverly J. Blachly, executor, 3348 NW. Skyline Blvd., Portland, Oreg. 97229

[21] Appl. No.: 967,902

[22] Filed: Dec. 11, 1978

[51] Int. Cl.³ ............................................. A61M 16/00
[52] U.S. Cl. ................................ 128/207.14; 128/136
[58] Field of Search ................... 128/208, 145.5, 145.6, 128/145.7, 145.8, 147, 136, 351, 202.28, 203.11, 205.13, 203.28, 205.17, 205.18, 207.14, 207.15

[56] References Cited

U.S. PATENT DOCUMENTS

| | | | |
|---|---|---|---|
| 1,270,565 | 6/1918 | Teter | 128/208 |
| 1,498,810 | 6/1924 | Poe | 128/207.14 X |
| 2,669,988 | 2/1954 | Carpenter | 128/136 |
| 2,882,893 | 4/1959 | Godfroy | 128/136 |
| 3,006,337 | 10/1961 | Aguado | 128/202.28 |
| 3,013,554 | 12/1961 | Safar et al. | 128/145.5 |
| 3,046,978 | 7/1962 | Lea | 128/205.13 |

*Primary Examiner*—Henry J. Recla
*Attorney, Agent, or Firm*—Chernoff & Vilhauer

[57] ABSTRACT

An oropharyngeal airway tube and bite block assembly having means for connection of a ventilatory resuscitator bag. The bite block provides an air-tight seal between the oropharyngeal airway tube and the gums, teeth, and lips of a patient which, in combination with conventional nostril occluding means, permits closed pulmonary ventilation of a patient without the need for a face mask nor endotracheal tube. The bite block properly locates and provides protection for the airway tube to provide an unobstructed air passage.

2 Claims, 4 Drawing Figures

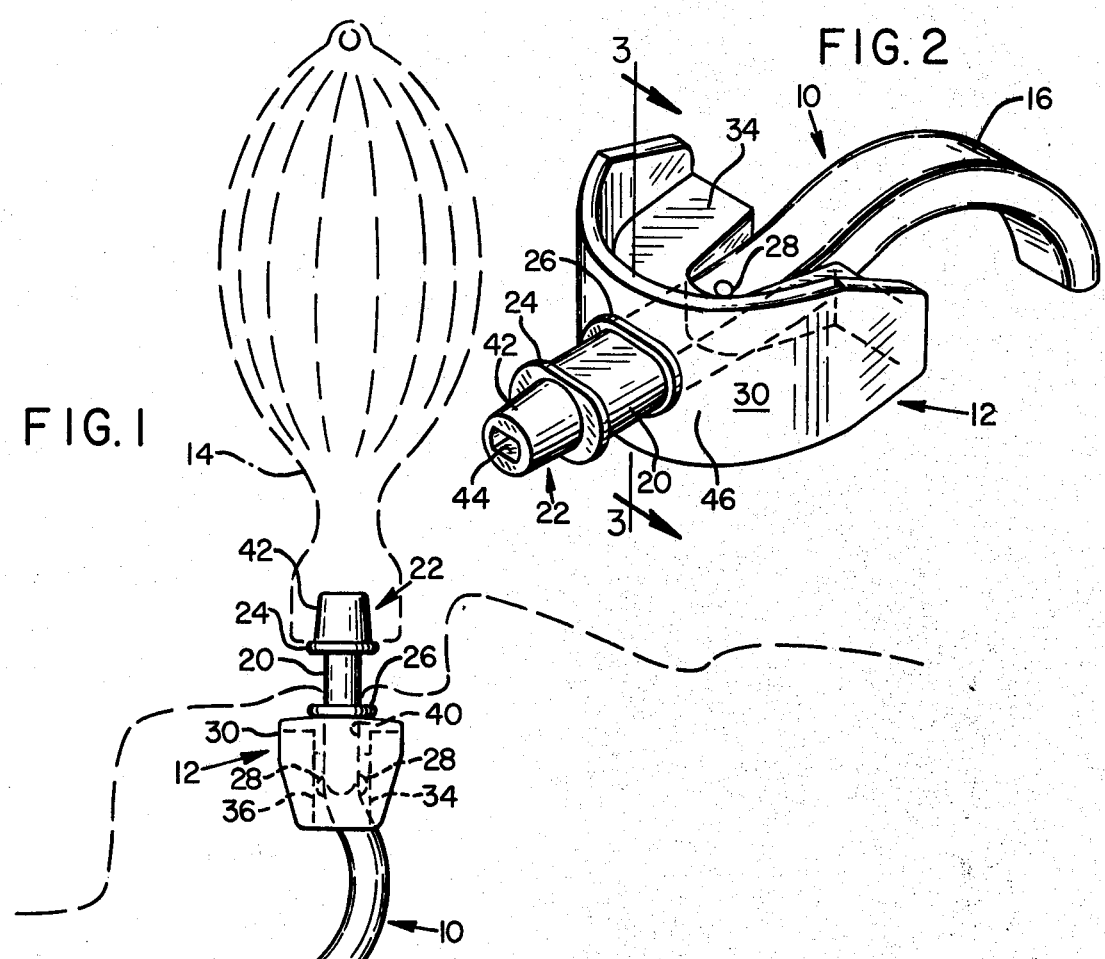
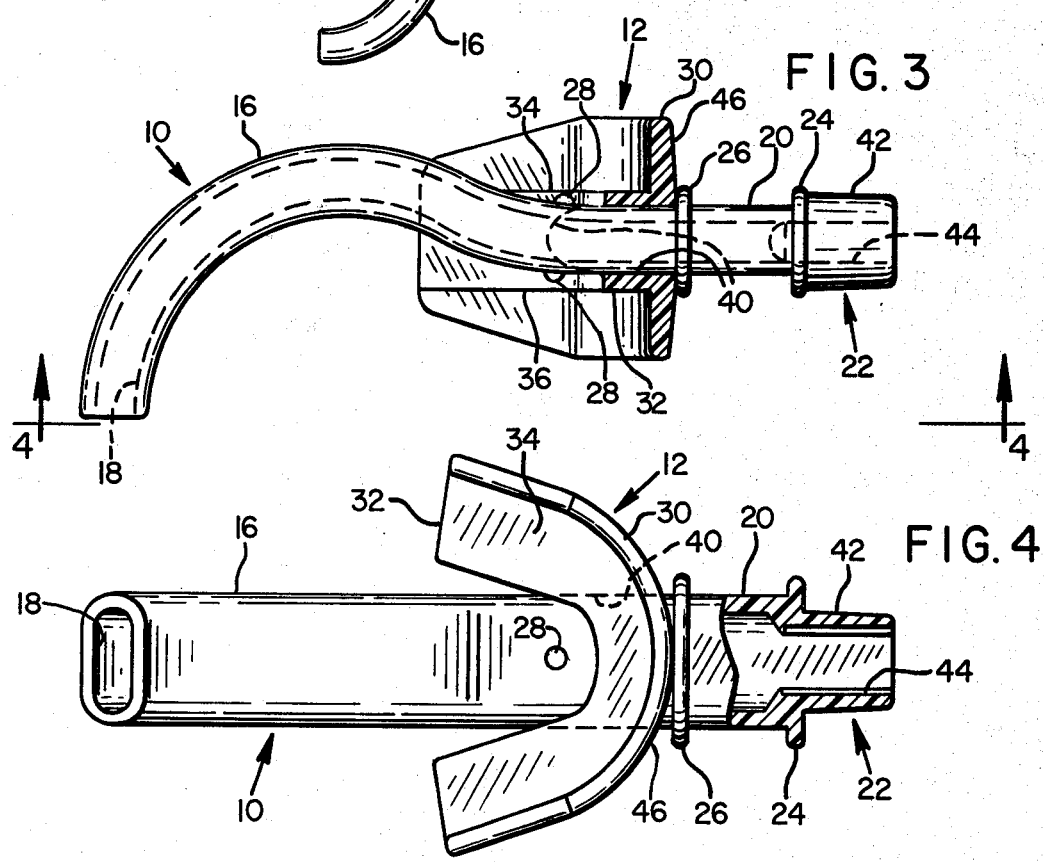

OROPHARYNGEAL AIRWAY AND BITE BLOCK ASSEMBLY AND METHOD OF USE FOR CLOSED PULMONARY VENTILATION

BACKGROUND OF THE INVENTION

This invention relates to improvements in means for providing closed artificial pulmonary ventilation to patients, such as during the administration of pressurized air for forced ventilation or resuscitation or during the administration of unpressurized oxygen or oxygen-enriched air where leakage to or from the atmosphere must be prevented because of the non-atmospheric nature (either due to pressure or composition) of the gases being administered. More particularly, the invention relates to a method and apparatus for providing closed pulmonary ventilation by means of an oropharyngeal airway in combination with a sealing bite block.

Conventionally, either a face mask or an endotracheal tube may be used as a means for providing closed ventilation by sealed means, allowing gases of predetermined mixture or pressure to be introduced or forced into the lungs. Either of these two conventional methods, however, has serious disadvantages.

The use of a mask to seal around oral and nasal openings to allow introduction of gases from a resuscitator may be somewhat frightening to patients who are in a semi-conscious state. Another common problem with the use of a mask is that it does not fit well on some patients, especially those who are edentulous, since there is less support of the external facial tissues for forming a seal around the edge of the mask, and therefore an undesirable amount of leakage, either from or to the atmosphere, occurs. Also, during use of a mask the tongue or lips of the patient may interfere with passage of air and prevent ventilation.

Endotracheal intubation provides the ideal system of closed pulmonary ventilation insofar as efficiency of ventilation is concerned, but it has the serious drawback that it is occasionally difficult to achieve, and that the patient may experience long-lasting residual hoarseness caused by irritation of the vocal cords by the endotracheal tube.

Use of an ordinary oropharyngeal airway tube avoids the problem or hoarseness, but again presents the problem of leakage, as there is no nasal or oral seal. Another common problem with the use of ordinary oropharyngeal airways is that a patient in convulsion, particularly that caused during electro-convulsive therapy, can bite down on the airway tube, occluding the air passage.

The Buttaravoli U.S. Pat. No. 3,809,079 describes a flexible face mask combined with an oropharyngeal airway. While this does provide a method of sealing around the nose and mouth of some patients so that closed pulmonary ventilation may be accomplished using an oropharyngeal airway, it still has all of the above mentioned disadvantages of use of a face mask in that it may cause fright in a semi-conscious patient, and gives no improvement over a mask alone in obtaining a sealing fit in edentulous patients.

Conventional bite block and airway tube assemblies, such as that shown in the Carpenter U.S. Pat. No. 2,669,988, have previously been used only to insure access of the oral passageway to atmospheric air (rather than to seal the oral passageway from atmospheric air as is the case with closed ventilation), and have not been capable of connection to ventilatory bags or other similar closed ventilation apparatus, as evidenced by the oval, rather than round, cross section at the exterior end of the airway tube.

What is therefore needed is a means for providing closed pulmonary ventilation of a patient without the difficulty and residual hoarseness associated with endotracheal intubation, and with better sealing than is available with face masks or conventional oropharyngeal airways while avoiding patient fright caused by having a mask placed over his or her face.

SUMMARY OF THE INVENTION

The present invention achieves the objectives and overcomes the disadvantages described above by providing a novel oropharyngeal airway and companion bite block assembly to provide a closed ventilation system, as an alternative to endotracheal intubation or the use of a face mask.

The oropharyngeal airway assembly of the invention, in its preferred embodiment, has a posterior airway tube portion having the same general configuration as conventional oropharyngeal tubes such as the Guedel airway, but an anterior tube portion which is modified so as to accommodate the standard connection to a ventilatory bag such as the Ambu resuscitator or other means for providing pressurized or enriched air of predetermined mixture. A bite block is fitted about the exterior of the airway tube between and comprises a tough, resilient U-shaped spacer block having vertically separated upper and lower tooth- or gum-engaging surfaces. A peripheral rim extends both above and below the spacer block to fit against the outer surfaces of the teeth or gums of the patient and inside the lips. An oval aperture extends through the base or central portion of the U-shaped spacer block, emerging between the laterally spaced sides of the U-shape. The airway tube is inserted through the aperture, forming a tight seal within the aperture and, when inserted into the patient's mouth, the posterior tube portion extends above the tongue to the upper throat, preventing the tongue from blocking the throat. The oval-shaped aperture, coupled with the resilient material of the bite block, is capable of matingly and frictionally accepting insertion of the airway while permitting limited longitudinal sliding of the airway tube with respect to the bite block for adjustment of the degree of insertion of the airway tube.

When the airway tube and bite block assembly have been thus properly placed in the patient's mouth and the nostrils occluded with conventional nostril occluding clips, a closed airway is provided by virtue of the oral seal between lips and bite block without the need for endotracheal intubation or face masks.

An annular shoulder around the anterior portion of the oropharyngeal tube limits the extent of insertion of the tube through the bite block, and a pair of small raised hemispherical areas located on the top and bottom, respectively, of the tube act as interference detents to hold the bite block and tube in the normal mated configuration to avoid unintentional withdrawal of the tube. The tube extends forward between the patient's lips, and a slightly tapered frustoconical connector or similar connector of substantially round cross section on the anterior portion of the tube sealingly mates with a standard ventilator or resuscitator bag for connecting the airway and bite block assembly to closed ventilating or resuscitating equipment.

A tight oral seal is provided by the airway and bite block assembly of the invention, even in the absence of teeth, and closed pulmonary ventilation of the patient is assured without the danger of atmospheric leakage or occlusion of the airway tube. The airway occlusion protection provided by the bite block also permits the use of a softer material for the airway tube to increase patient comfort, by reducing the necessity for stiffness of the airway tube to resist compression from tooth or gum pressure.

It is therefore a primary objective of the present invention to provide an improved method and apparatus for closed pulmonary ventilation of a patient requiring the use of neither a face mask nor endotracheal tube.

It is another principal objective of the invention to provide a method and apparatus for closed pulmonary ventilation which creates a more effective seal in edentulous patients than does a face mask.

The foregoing and other objectives, features, and advantages of the invention will be more readily understood upon consideration of the following detailed description of the invention, taken in conjunction with the accompanying drawings.

BRIEF DESCRIPTION OF THE DRAWINGS

FIG. 1 is a simplified view of an exemplary oropharyngeal airway tube and bite block assembly embodying the present invention in place in the mouth of a reclining patient, with a ventilatory bag attached to the airway tube.

FIG. 2 is a perspective view of the airway tube and bite block assembly of FIG. 1.

FIG. 3 is a partially sectional side view of the airway tube and bite block assembly of FIG. 1.

FIG. 4 is a partially sectional bottom view of the airway tube and bite block assembly of FIG. 1.

DESCRIPTION OF THE PREFERRED EMBODIMENT

Referring to FIG. 1, an exemplary oropharyngeal airway tube 10 and associated bite block 12 may be seen in position for closed pulmonary ventilation of a reclining patient, with a ventilatory bag 14 attached to the oropharyngeal airway tube 10. With the airway tube and bite block assembly of the invention thus positioned within a patient's mouth, and the nostrils occluded by any conventional means such as a nostril occluding clip (not shown), closed pulmonary ventilation of the patient is made possible by the seal around the airway 10 formed by the bite block 12 with the lips of the patient.

Referring to FIGS. 2, 3 and 4, the airway tube 10 and bite block 12 are shown in perspective view with the airway tube in its normal position inserted through the bite block. The oropharyngeal airway tube 10 comprises a downwardly curved posterior tongue depressor portion 16 including an end opening 18, a straight anterior portion 20 and a connector 22, by means of which the ventilatory bag 14 may be attached.

The anterior portion 20 of the airway tube includes an annular shoulder 24 at the junction between the connector 22 and the anterior portion 20. An annular shoulder positioning stop 26 located on the anterior portion, rearwardly of the annular shoulder 24, prevents insertion of the airway tube 10 too far into the bite block 12, and a pair of protruding hemispherical interference detents 28 located respectively on the top and bottom of the airway tube resist unwanted withdrawal of the airway tube from the bite block 12, while still permitting the airway tube to be partially withdrawn if desired for adjustment to improve patient comfort.

The bite block 12 comprises a U-shaped spacer 32 having a peripheral U-shaped rim 30 extending both above and below the spacer 32, the spacer and rim each being formed with the base or central portion of the "U" at the front of the bite block and the laterally spaced sides "U" extending longitudinally rearwardly. A preferred type of bite block is that disclosed in Blachly U.S. Pat. No. 4,122,936, the disclosure of which is incorporated herein by this reference. Upper and lower tooth- or gum-engaging surfaces 34 and 36 respectively located on the spacer 32 in this type of bite block maintain separation between a patient's upper and lower jaws. An airway tube-receiving oval aperture 40 extends from front to back through the base or central portion of the peripheral rim 30 and the spacer 32.

The connector 22 comprises a frusto-conical surface 42, or similar surface of substantially round cross section, of the appropriate mating size to connect detachably to the round connectors or hoses of standard closed ventilatory apparatus such as the Ambu resuscitator bag, and includes an orifice 44 which communicates with the interior of the airway tube 10.

The airway tube and bite block assembly of the present invention are assembled for use by inserting the posterior portion 16 of the airway tube 10 sealingly into the tube-receiving aperture 40 of the bite block 12 from a front surface 46 of the bite block and pushing the airway tube 10 through the tube-receiving aperture until the annular shoulder positioning stop 26 abuts against the front surface 46 of the bite block and the detents 28 have passed beyond the rearward edge of the central portion of the U-shaped spacer 32. The assembled airway tube and bite block are inserted into the mouth of the patient so that the patient's teeth or gums engage the upper and lower gum-engaging surfaces 34 and 36 and the peripheral rim 30 of the bite block is outside the teeth or gums and inside the lips of the patient. The anterior portion 20 of the airway tube is allowed to extend outward beyond the lips of the patient, while the posterior portion 16 of the airway tube extends over the patient's tongue into the upper throat. The rounded end opening 18 helps to reduce patient discomfort caused by the presence of the airway tube, while the position of the bite block, and of the airway tube within the bite block, determine the depth of insertion of the airway in the patient's throat.

The bite block 12 may be made of somewhat flexible and resilient material, the amount of flexibility and resilience depending upon the use for which the bite block and airway are intended, as the bite block must protect the airway tube 10 form being pinched to the point where air flow is impeded, should the patient bite down. Thus, for use during electro-convulsive therapy, a harder, less resilient block is needed than may be used for normal ventilation or anesthesia procedures where crushing of the airway tube is less likely. The protective effect of the bite block allows the airway tube 10 to be manufactured from somewhat soft and resilient material. Although a certain amount of stiffness must be retained in the airway tube, the tube may be much softer and more resilient, and therefore more comfortable, than if it must of itself resist being crushed by the mandibular contractions of a patient in convulsion.

When the bite block and airway tube assembly has been inserted into the mouth of a patient in the above-described manner, a device such as the ventilatory bag 14 which is part of a mechanical ventilator system, resuscitator or similar closed ventilation system, is attached and operated in the appropriate manner. The bite block and airway combination insure against leakage, between the interior of the patient's mouth and the atmosphere, providing a seal between the rim 30 and patient's lips, regardless of whether or not the patient is edentulous, which may be impossible to obtain using a mask.

While the airway tube described above preferably includes the interference detents 28 to retain the airway tube at a predetermined position within the bite block, these detents may be omitted, allowing the position of the airway tube within the bite block to be more easily adjusted, permitting one size of airway tube to be used with minimum discomfort for patients of widely varying size and age. The airway and bite block may also be a unitary construction, although this limits the range of adjustment of the depth of insertion of the posterior portion of the airway tube into the patient's throat, and is therefore less conducive to patient comfort.

The terms and expressions which have been employed in the foregoing specification are used therein as terms of description and not of limitation, and there is no intention, in the use of such terms and expressions, of excluding equivalents of the features shown and described or portions thereof, it being recognized that the scope of the invention is defined and limited only by the claims which follow.

What is claimed is:

1. A combination oropharyngeal airway and bite block assembly for use in providing closed pulmonary ventilation of a patient, comprising:
   (a) an oropharyngeal airway tube having means defining a curved tubular posterior portion, for introduction through the mouth into the upper throat of a patient, a tubular anterior portion connected to said posterior portion and tubular connector means connected to said anterior portion for detachably and sealingly connecting said airway tube to a closed ventilation apparatus;
   (b) a U-shaped bite block in engagement with said airway tube for preventing occlusion of the airway tube when the assembly is inserted in the patient's mouth, said bite block having a central aperture, said airway tube and said aperture having frictionally mating surface means for permitting said airway tube and said aperture to frictionally and sealingly engage one another in a plurality of positions along the length of said airway tube, thereby permitting slidable adjustment of said airway tube with respect to said bite block;
   (c) positioning stop means located on said anterior portion of said airway tube for limiting rearward motion of said airway tube within said aperture of said bite block; and
   (d) detent means including a plurality of generally hemispherical protrusions located on said posterior portion of said airway tube, the distance between said forward stop means and detent means being greater than the thickness of said bite block from front to back along said central aperture, whereby said detent means limits the forward movement of said airway tube within said aperture of said bite block.

2. The combination of claim 1 wherein said airway tube is of pliable resilient material and said bite block is of harder resilient material, said airway tube being sufficiently stiff to resist collapsing within the upper throat of a patient, and said bite block being sufficiently hard to prevent the patient from occluding said airway tube by biting.

* * * * *

UNITED STATES PATENT AND TRADEMARK OFFICE
CERTIFICATE OF CORRECTION

PATENT NO. : 4,270,531

DATED : June 2, 1981

INVENTOR(S) : Paul H. Blachly, deceased By Beverly J. Blachly, executor

It is certified that error appears in the above-identified patent and that said Letters Patent are hereby corrected as shown below:

Col. 2, Line 61    Change "frustoconical" to --frusto-conical".

Col. 4, Line 6     After "sides" insert the words --of the--;

Col. 4, Line 51    Change "form" to --from--.

Col. 5, Line 16    Change "a" to --of--.

Signed and Sealed this

Seventeenth Day of August 1982

[SEAL]

Attest:

GERALD J. MOSSINGHOFF

Attesting Officer    Commissioner of Patents and Trademarks